US00PP25075P2

(12) United States Plant Patent
Huisman

(10) Patent No.: US PP25,075 P2
(45) Date of Patent: Nov. 18, 2014

(54) ***HYDRANGEA* PLANT NAMED 'SILVER LINING'**

(50) Latin Name: ***Hydrangea anomala* subsp. *petiolaris***
Varietal Denomination: Silver Lining

(71) Applicant: Nico Huisman, Boskoop (NL)

(72) Inventor: Nico Huisman, Boskoop (NL)

( * ) Notice: Subject to any disclaimer, the term of this patent is extended or adjusted under 35 U.S.C. 154(b) by 168 days.

(21) Appl. No.: 13/694,091

(22) Filed: Oct. 30, 2012

(51) Int. Cl.
*A01H 5/00* (2006.01)

(52) U.S. Cl.
USPC ..... Plt./250

(58) Field of Classification Search
CPC ..... A01H 5/02; A01H 5/00; A01H 1/02
USPC ..... Plt./250
See application file for complete search history.

(56) References Cited

PUBLICATIONS

Upov Pluto Plant Variety Database 201405023, retrieved on May 29, 2014, retrieved from Internet at <http://www.upov.int/pluto/en/index.jsp> for *Hydrangea* 'Silver Lining', one page.*

* cited by examiner

*Primary Examiner* — June Hwu
(74) *Attorney, Agent, or Firm* — Penny J. Aguirre

(57) ABSTRACT

A new cultivar of *Hydrangea anomala* subsp. *petiolaris* named 'Silver Lining' that is characterized by its variegated foliage with green centers and white margins, its stems that are brownish-orange in color when mature and its leaf buds that are light green in color.

3 Drawing Sheets

Genus/species: *Hydrangea anomala* subsp. *petiolaris*.
Varietal denomination: 'Silver Lining'.

BACKGROUND OF THE INVENTION

The present invention relates to a new and distinct cultivar of *Hydrangea anomala* subsp. *petiolaris* and will be referred to hereafter by its cultivar name, 'Silver Lining'. 'Silver Lining' represents a new climbing *Hydrangea* grown for landscape use.

The Inventor discovered the new cultivar in 2005 as a naturally occurring branch mutation of *Hydrangea anomala* subsp. *petiolaris* 'Firefly' (U.S. Plant Pat. No. 11,038, also known as 'Miranda') that was growing in a container at his nursery in Boskoop, The Netherlands.

Asexual reproduction of the new cultivar was first accomplished by softwood stem cuttings in Boskoop, The Netherlands in 2006 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Silver Lining' as a unique cultivar of *Hydrangea*.

1. 'Silver Lining' exhibits variegated foliage with green centers and white margins.
2. 'Silver Lining' exhibits stems that are brownish-orange in color when mature.
3. 'Silver Lining' exhibits leaf buds that are light green in color.

'Firefly', the parent plant of 'Silver Lining' differs from 'Silver Lining' in having foliage that is variegated with green centers and golden yellow margins. The new cultivar of

*Hydrangea* can be most closely compared to other cultivars of *Hydrangea anomala* subsp. *petiolaris* which are similar to 'Silver Lining' in having uniquely colored foliage; 'Kuga Vareigated' (U.S. Plant Pat. No. 13,247), 'Kasai' (U.S. Plant Pat. No. 13,845), and 'Buttercup' (not patented). 'Kuga Vareigated' differs from 'Silver Lining' in having foliage that is speckled green and white. 'Kasai' differs from 'Silver Lining' in having foliage that emerges white with green stippling and becomes green with white margins and some white stippling. 'Buttercup' differs from 'Silver Lining' in having foliage that is non-variegated and yellow in color.

BRIEF DESCRIPTION OF THE DRAWINGS

The accompanying photographs were taken of a one year-old plant of 'Silver Lining' as grown outdoors in a 17-cm container in Boskoop, The Netherlands.

The photograph in FIG. 1 provides a side-view of a plant of 'Silver Lining'.

Figure 1:
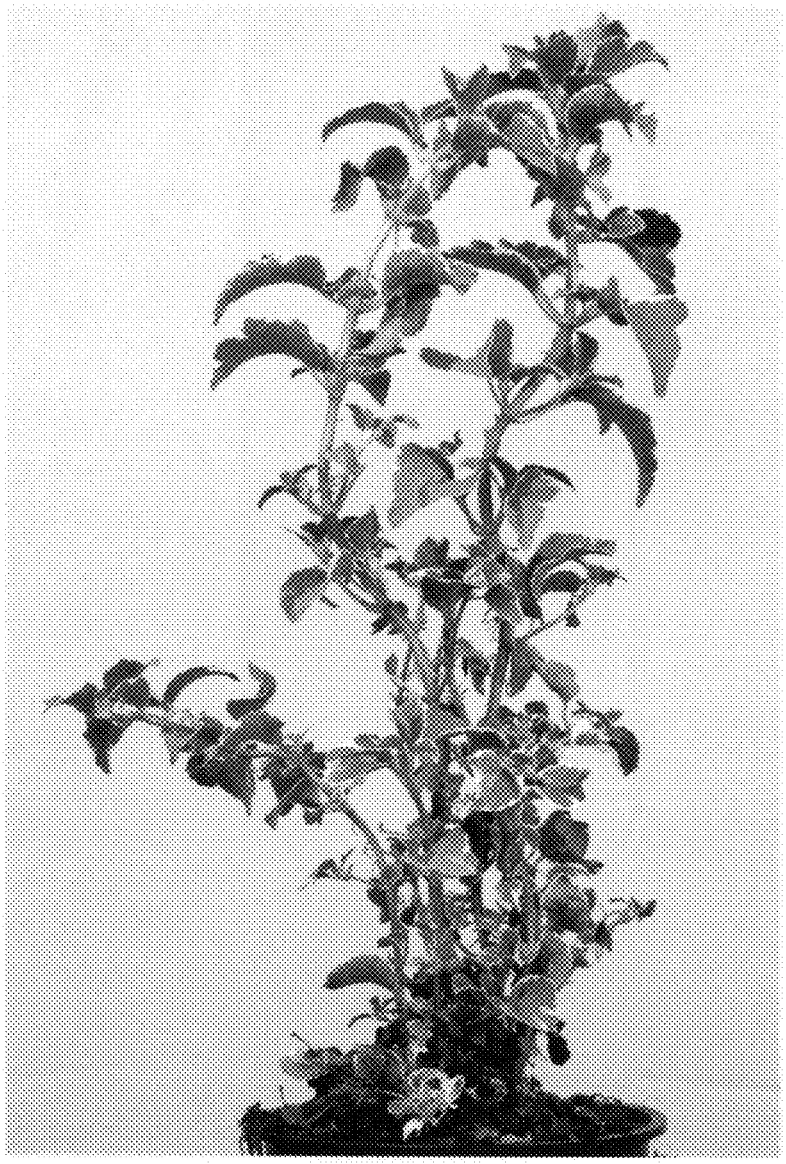
Figure 2:
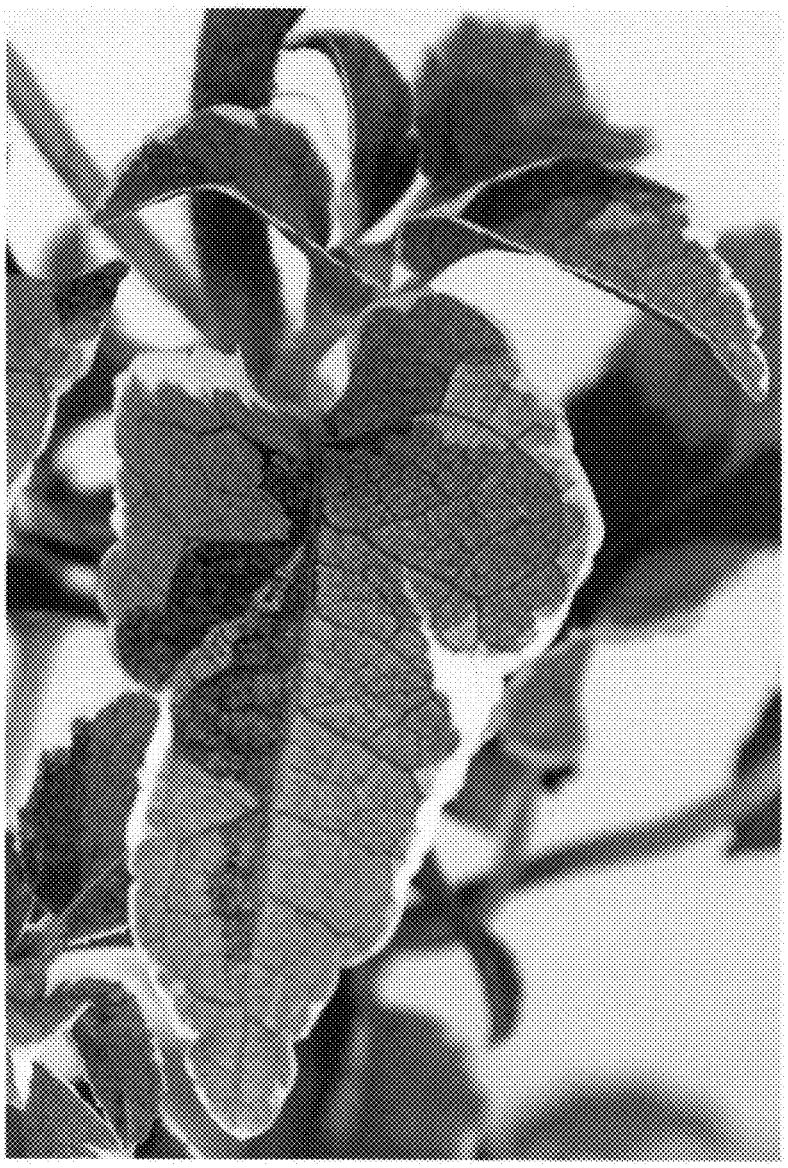

The photograph in FIG. 2 provides a close-up view of a leaf of 'Silver Lining'.

Figure 3:
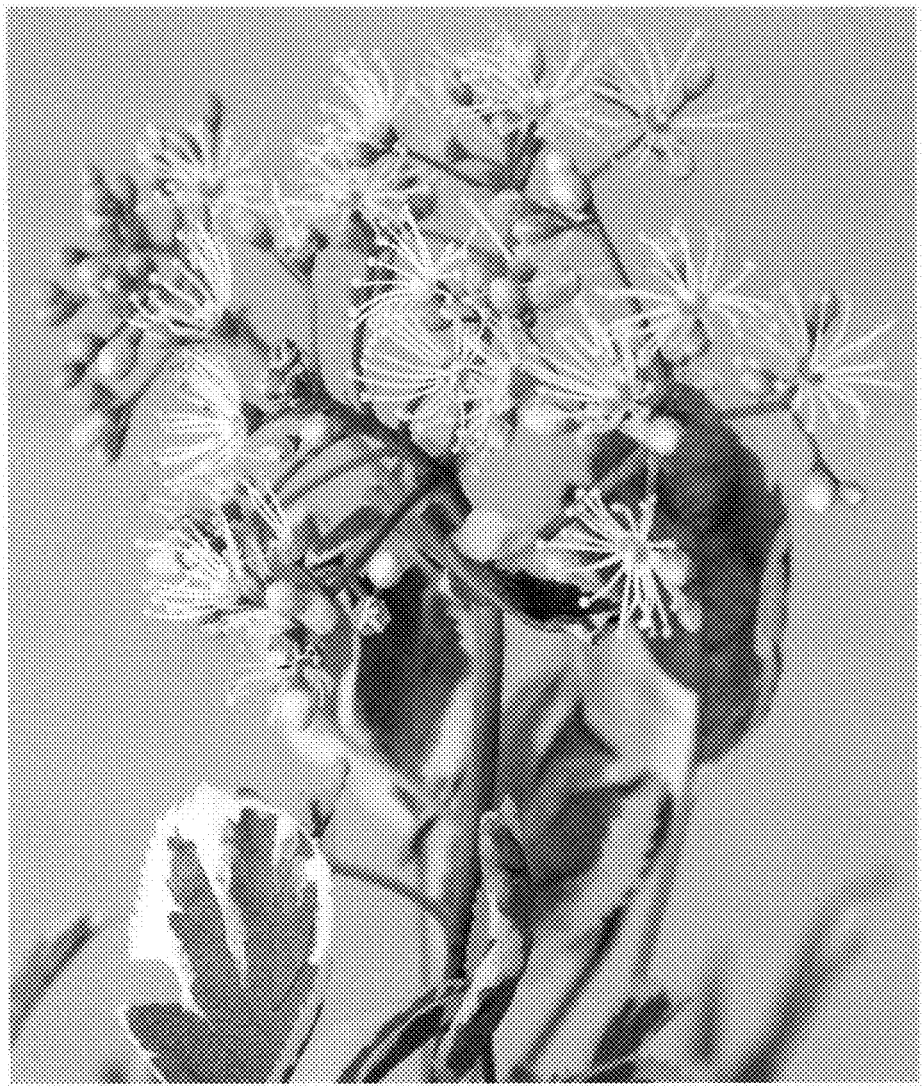

The photograph in FIG. 3 provides a close-up view of an inflorescence of 'Silver Lining' (only fertile flowers are open).

The colors in the photographs are as close as possible with the digital photography and printing techniques utilized and the color codes in the detailed botanical description accurately describe the new *Hydrangea*.

BOTANICAL DESCRIPTION OF THE PLANT

The following is a detailed description of one year-old plants as grown in 17-cm containers outdoors in Boskoop, The Netherlands. The plants were grown under average day temperatures of 14° C. to 28° C. and average night temperatures of 8° C. to 17° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Late spring to early summer in The Netherlands.

*Plant habit*.—Broadly upright, deciduous shrub.

*Height and spread*.—Reaches about 47.4 cm in height and 27 cm in diameter (one year-old plant).

*Cold hardiness*.—At least to U.S.D.A. Zone 5.

*Diseases resistance*.—Not more susceptible or resistant to diseases than other *Hydrangea anomala* subsp. *petiolaris* varieties.

*Root description*.—Fine.

*Propagation*.—Softwood stem cuttings.

*Growth rate and vigor*.—Moderate.

Stem description:

*Stem shape*.—Round.

*Stem color*.—Young shoots; 145D, older bark; ranging between N170A to N170B to N199D.

*Stem size*.—Main branches; average of 27.3 cm in length and 4 mm diameter, lateral branches; 5.7 cm in length and 2 mm in diameter.

*Stem surface*.—Slightly glossy, covered with soft short hairs average length 1 mm in length and 156D in color.

*Branching*.—Moderately branching, average of 15 lateral branches per plant, an average of 7 main branches growing from the base, the two thickest main branches are further branched into an average of 6 lateral branches per main branch.

*Internode length*.—Average of 3.4 cm.

Foliage description:

*Leaf shape*.—Ovate to broad ovate to oblong and slightly carinate.

*Leaf arrangement*.—Opposite.

*Leaf division*.—Simple.

*Leaf number*.—Main branches; average of 16 (8 pairs), lateral branches; 4 (2 pairs) per lateral branch.

*Leaf buds*.—Ovate in shape, an average of 8 mm in length and width, 138C in color.

*Leaf base*.—Obtuse.

*Leaf apex*.—Acute to bluntly acute.

*Leaf margins*.—Irregular crenate to irregular undeep angulate.

*Leaf venation*.—Pinnate, upper surface; 143B in color, lower surface; 147C in color.

*Leaf size*.—Average of 5.2 cm in length and 1.2 cm in width.

*Leaf attachment*.—Petiolate.

*Leaf surface*.—Upper and lower surface; moderately rugose and slightly leathery, sparsely covered with short adpressed hairs on main vein, average of 0.5 mm in length and 155A in color.

*Leaf color*.—Young foliage upper surface; 189A, occasionally areas of 139A, irregularly and narrowly margined 150D, young foliage lower surface; 191A, irregularly and narrowly margined 155A, mature foliage upper surface; 191A, occasionally areas of 139A and 147A, irregularly and narrowly margined a color between 155A and 157D, mature foliage lower surface; 191A to 191B, irregularly and narrowly margined 155A, fall color (upper and lower surface); centers 160A with margins 162A.

*Petioles*.—Average of 1.2 cm in length, 2 mm in width and 144B in color, surface is pubescent with soft hairs.

Inflorescence description:

*Inflorescence type*.—Modified lacecap with primiarly fertile flowers with a few sterile flowers.

*Lastingness of inflorescence*.—Persistent with color lasting about 3 weeks.

*Inflorescence number*.—One per lateral or sublateral stem.

*Inflorescence size*.—Average of 5.2 cm in height and 14.8 cm in diameter.

*Flower number*.—An average of 240 fertile flowers and 5 sterile flowers per inflorescence.

*Flower fragrance*.—Moderately strong, sweet and pleasant.

*Flower aspect*.—Upright and slightly outward.

*Flower size*.—Sterile flowers; rotate, average of 2.5 cm in diameter and 0.9 cm in depth, fertile flowers; rotate, average of 1.6 mm in diameter and 0.8 mm in depth.

*Flower buds*.—Fertile and sterile flowers; 0.5 cm in length and 0.35 cm in diameter, color is 145B, base 145A.

*Peduncles*.—Average of 6.8 cm in length and 0.3 cm in diameter, held at an average angle of 0°, secondary peduncles held at an average angle of 75° to main peduncle, moderately strong and 145B in color.

*Pedicels*.—Fertile flowers; an average of 0.3 cm in length and 0.1 mm in diameter, held at an average angle of 30° to peduncle, moderately strong in strength and 145B in color, sterile flowers; an average of 3.2 cm in length and 0.1 cm in diameter, held at an average angle of 30° to peduncle, moderately strong in strength and 145B in color.

*Petals*.—Not present in sterile, fertile flowers have been transformed into a "cap", forming the upper half of the flower bud, the cap is dropped when the flower opens, average of 3 mm in length and 3 mm in diameter and 150D in color.

*Sepals*.—Fertile flowers; average of 5, rotate in arrangement, sepals are fused into a campanulate shape, both surfaces smooth and matte, short triangular in shape, margin is entire, tip broad acute, base fused into campanulate shape, an average of 1 mm in length and 2 mm in width, color; young upper and lower surface; 145A, mature upper and lower surface; 145B, sterile flowers; average of 4, rotate in arrangement, both surfaces smooth, slightly rugose and matte, broad ovate in shape, margin is entire, tip rounded, base attenuate, an average of 1.3 cm in length and 1.2 cm in width, color; young and mature upper and lower surface; 145C, irregulaly margined 155D.

Reproductive organs:

*Stamens*.—Fertile flowers average of 20, sterile flowers average of 8, fertile and sterile flowers; anther is about 1 mm in length and 155A in color, filament is an average of 6 mm in length and NN155D in color, pollen is low in quantity and 4D in color.

*Pistils*.—Fertile flowers; Average of 2, average of 2 mm in length, style is an average of 1 mm in length and NN155C in color, stigma is club-shaped, decurrent and NN155C in color, ovary is 145A in color.

*Fruit and seed*.—None observed.

It is claimed:

1. A new and distinct cultivar of *Hydrangea* plant named 'Silver Lining' substantially as herein illustrated and described.

* * * * *